US00PP09636P

United States Patent [19]

Meilland

[11] Patent Number: Plant 9,636

[45] Date of Patent: Aug. 27, 1996

[54] HYBRID TEA ROSE PLANT NAMED MEIBOLNAY

[75] Inventor: Alain A. Meilland, Antibes, France

[73] Assignee: The Conard-Pyle Company, West Grove, Pa.

[21] Appl. No.: 492,450

[22] Filed: Jun. 19, 1995

[51] Int. Cl.[6] ..... A01H 5/00

[52] U.S. Cl. ..... Plt./20

[58] Field of Search ..... Plt./20, 21

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which abundantly forms attractive very large double blossoms that are deep velvet red in coloration. Such blossoms are long-lasting when cut and placed in a vase and exhibit very good petal-drop characteristics. The plant exhibits large erect sturdy stems and forms large medium green foliage (as illustrated). The new variety is particularly well suited for cut flower production under greenhouse growing conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the artificial pollination of the 'Deladel' variety (U.S. Plant Pat. No. 4,391) and the 'Korlingo' variety (U.S. Plant Pat. No. 5,846). The male parent (i.e., the pollen parent) was the 'Meibuito' variety (non-patented in the United States). The parentage of the new variety can be summarized as follows:

('Deladel'×'Korlingo')×'Meibuito'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive very large long-lasting deep velvet red blossoms,
(b) forms long erect strong stems,
(c) forms large medium green foliage, and
(d) is particularly well suited for cut flower production.

The new variety well meets the needs of the horticultural industry and is particularly well adapted for cut flower production under greenhouse growing conditions.

The new variety has been found to undergo asexual propagation in France by a number of routes, including budding, grafting, and cuttage. Asexual propagation by the above-mentioned technique in France has shown that the characteristics of the new variety are stable and are strictly transmissible by such asexual propagation from one generation to another.

The new variety has been named the 'Meibolnay' variety.

The new variety will be marketed under the Top Secret trademark.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during September while budded on *Rosa indica* understock and growing in greenhouses at Le Cannet des Maures, Var, France.

DETAILED DESCRIPTION

Figures 1, 2, 3, 4, 5, 6, 7, 8, 9, 10, 11, 12, 13, 14, 15:
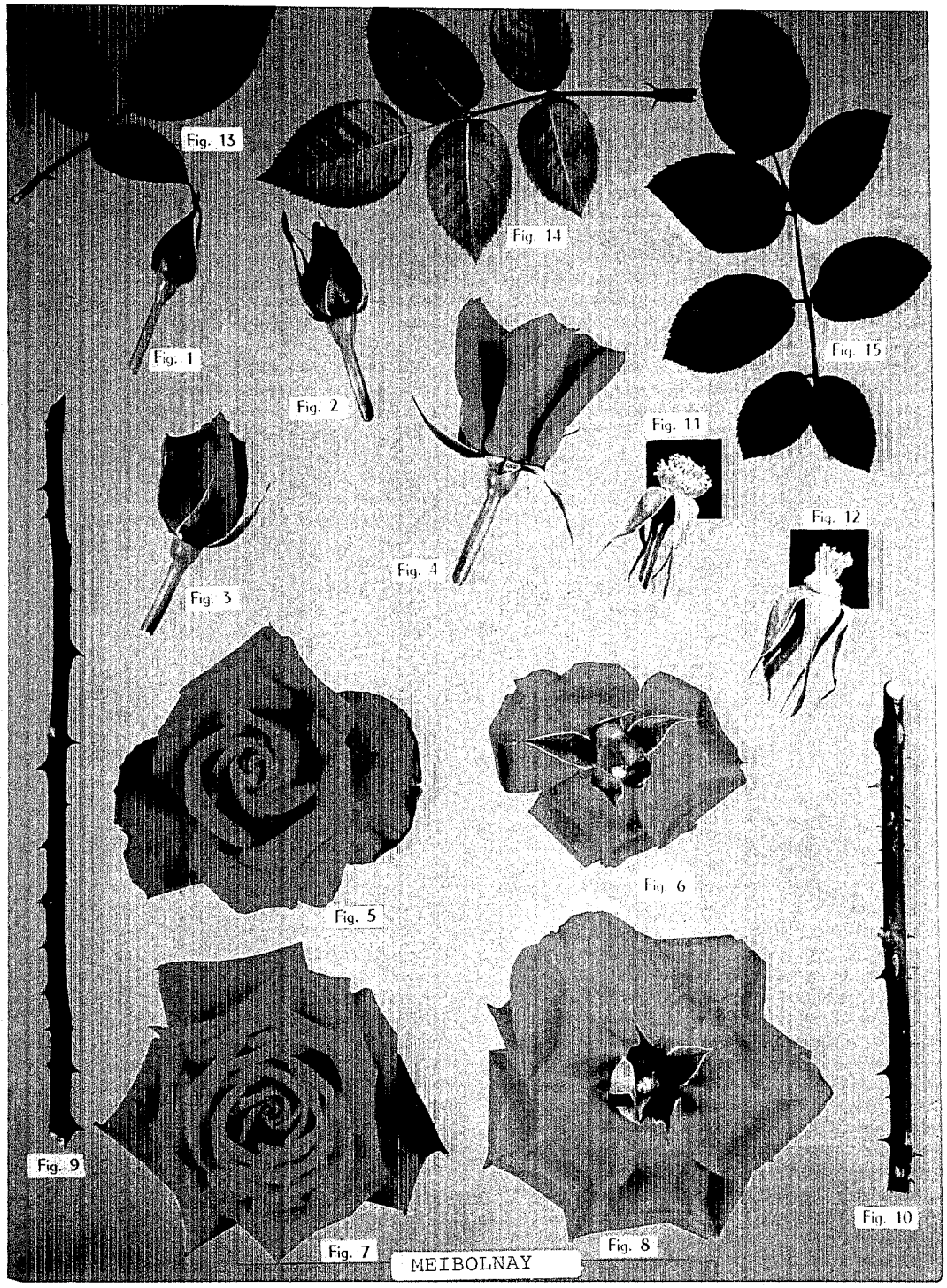
FIG. 1 illustrates a specimen of a floral bud before the opening of the sepals.
FIG. 2 illustrates a specimen of a floral bud at the opening of the sepals.
FIG. 3 illustrates a specimen of a floral bud at the opening of the petals.
FIG. 4 illustrates a specimen of a flower in the course of opening.
FIG. 5 illustrates a specimen of an open flower—plan view—obverse.
FIG. 6 illustrates a specimen of an open flower — plan view — reverse.
FIG. 7 illustrates a specimen of a fully open flower—plan view—obverse.
FIG. 8 illustrates a specimen of a fully open flower—plan view—reverse.
FIG. 9 illustrates a specimen of a flowering stem.
FIG. 10 illustrates a specimen of a main branch.
FIG. 11 illustrates a specimen of a floral receptacle showing the arrangement of the stamens and pistils.
FIG. 12 illustrates a specimen of a floral receptacle showing the arrangement of the pistils (stamens removed)
FIG. 13 illustrates a specimen of a leaf with three leaflets—plan view—upper surface.
FIG. 14 illustrates specimens of a leaf with five leaflets—plan view—under surface.
FIG. 15 illustrates a specimen of a leaf with seven leaflets—plan view—upper surface.

The chart used in the identification of the colors is that of The Royal Horticultural Society (R.H.S. Colour Chart). The description is based on the observation of two year-old plants while budded on *Rosa indica* understock and growing in greenhouse at Le Cannet des Maures, Var, France. The coloration in common terms precedes reference to the chart.

Class: Hybrid Tea.

Plant:

*Height.*—When the plant is pruned to a height of 85 cm., floral stems of approximately 80 to 90 cm. in length commonly are formed.

*Habit.*—Erect.

Branches:

*Color.*—Young stems: Agathia Green, Green Group 142B. Adult wood: medium green, Green Group 138A.

*Thorns.*—Size: small. Quantity: few. Color: greenish, Green Group 139D, and suffused with Greyed-Red Group 182D.

Leaves:

*Stipules.*—Adnate, pectinate, somewhat large and linear.

Petioles.—Upper surface: striped reddish brown, Greyed-Red Group 180A, on young foliage, and medium green, Green Group 137B, on adult foliage with slightly glandular edges. Under surface: light green, Green Group 143C, and widely suffused with Greyed-Red Group 180A on young foliage, and light green, Green Group 143C, on adult foliage.

*Leaflets.*—Number: 3, 5 (most often), and 7. Shape: elliptic. Serration: simple and regular. Texture: consistent. General appearance: dense, and glossy. Color (young foliage): Upper surface: light green, Green Group 141C. Under surface: light green, Yellow-Green Group 146D. Color (adult foliage): Upper surface: medium green, Green Group 136B. Under surface: medium green, Green Group 138A.

Inflorescence:

*Number of flowers.*—Usually one per stem. Approximately 130 to 150 flower/m.$^2$ commonly are formed per year.

Peduncle.—Generally lighter green than the remaining portion of the stem. Hairs and prickles commonly are absent. The length is approximately 10 cm. on average.

*Sepals.*—Upper surface: tomentose, commonly lack foliar appendages and light green in coloration. Under surface: light green, commonly lack foliar appendages and smooth.

*Buds.*—Shape: conical. Length: approximately 5 to 7 cm. on average. Size: large. Color upon opening: Upper surface: Cardinal Red, Red Group 53A. Under surface: Cardinal Red, Red Group 53A.

*Flower.*—Shape: double and cup-shaped with slightly pointed center. Diameter: approximaely 13 to 15 cm. on average. Color (when opening begins): Upper surface: Guardsman Red, Red Group 45A. Under surface: Guardsman Red, Red Group 45A. Color (when blooming): Upper surface: Guardsman Red, Red Group 45A. Under surface: Strawberry Red, Red Group 46B. Color (at end of opening): Upper surface: Post office Red, Red Group 45B. Under surface: Strawberry Red, Red Group 46B. Fragrance: none. Lasting quality: Approximately 12 days on average when cut and placed in a vase and approximately 16 days on average on the plant. Petal shape: rounded with reflexed edges when the blossoms mature. Petal number: approximately 37 to 41 on average. Petal drop: very good with petals commonly detaching cleanly upon full maturity. Stamen number: approximately 220 on average. Anthers: normal and light yellow to orange in coloration. Filaments: reddish in coloration. Pistils: approximately 210 on average. Stigmas: strawlike in coloration. Styles: rosy in coloration. Receptacle: generally lighter green in coloration than the peduncle. Hips and seeds: are formed.

Development:

*Vegetation.*—Very strong.

*Blooming.*—Abundant and highly productive in the substantial absence of blind wood.

*Aptitude to bear fruit.*—Medium.

*Resistance to diseases.*—Very good. Such disease resistance is above average with respect to diseases commonly encountered under greenhouse growing conditions, such as powdery mildew and downy mildew.

I claim:

1. A new and distinct variety of Hybrid Tea rose plant characterized by the following combination of characteristics:

(a) forms in abundance attractive very large long-lasting deep velvet red blossoms,
(b) forms long erect strong stems,
(c) forms large medium green foliage, and
(d) is particularly well suited for cut flower production;

substantially as herein shown and described.

* * * * *

MEIBOLNAY